(12) United States Patent
Beeckler (10) Patent No.: US 10,918,437 B2
(45) Date of Patent: *Feb. 16, 2021

(54) CATHETER WITH COAXIAL THERMOCOUPLE

(71) Applicant: BIOSENSE WEBSTER (ISRAEL) LTD., Yokneam (IL)

(72) Inventor: Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,702

(22) Filed: Apr. 3, 2019

(65) Prior Publication Data

US 2019/0223952 A1 Jul. 25, 2019

Related U.S. Application Data

(63) Continuation of application No. 14/714,904, filed on May 18, 2015, now Pat. No. 10,285,754.

(51) Int. Cl.
*A61B 18/14* (2006.01)
*G01K 7/06* (2006.01)
(Continued)

(52) U.S. Cl.
CPC ............ *A61B 18/1492* (2013.01); *G01K 7/06* (2013.01); *G01K 13/002* (2013.01); *H01B 1/026* (2013.01);
(Continued)

(58) Field of Classification Search
CPC ...... A61B 18/1492; A61B 2018/00077; A61B 2018/00083; A61B 2018/00351;
(Continued)

(56) References Cited

U.S. PATENT DOCUMENTS 3,343,589 A 9/1967 Holzl
4,408,088 A 10/1983 Foote
(Continued)

FOREIGN PATENT DOCUMENTS

CN 101539095 A 9/2009
CN 201950084 U 8/2011
(Continued)

OTHER PUBLICATIONS

European Search Report dated Sep. 22, 2016 from corresponding European Patent Application No. 16169868.3.
(Continued)

*Primary Examiner* — Michael F Peffley
(74) *Attorney, Agent, or Firm* — Frost Brown Todd LLC (57) ABSTRACT

An improved thermocouple includes a drawn coaxial thermocouple wire pair having a more precise "hot" junction at which a first and second metallic material electrically connect with each other for measuring temperature. Adapted for use with an electrophysiologic catheter, the improved thermocouple comprising an elongated body having a proximal end and a distal end. The body includes a core of a first metallic material, a first coaxial layer of ceramic material, and a second coaxial layer of a second metallic material. The thermocouple further includes a solder cap on the distal end, the solder cap electrically connecting the core and the second layer at the distal end. A method of manufacturing includes drawing the body through a die, and applying solder on a distal end of the body to electrically connect the two metallic materials at the distal end.

20 Claims, 7 Drawing Sheets

(51) Int. Cl.
   *G01K 13/00* (2021.01)
   *H01B 1/02* (2006.01)
   *H01B 3/12* (2006.01)
   *H01B 7/17* (2006.01)
   *A61B 18/00* (2006.01)

(52) U.S. Cl.
   CPC ............... *H01B 3/12* (2013.01); *H01B 7/17* (2013.01); *A61B 2018/00077* (2013.01); *A61B 2018/00083* (2013.01); *A61B 2018/00351* (2013.01); *A61B 2018/00577* (2013.01); *A61B 2018/00821* (2013.01)

(58) Field of Classification Search
   CPC  A61B 2018/00577; A61B 2018/00821; B21C 1/00; G01K 13/002; G01K 7/06; H01B 1/026; H01B 2/12
   See application file for complete search history.

(56) References Cited

U.S. PATENT DOCUMENTS

| | | | |
|---|---|---|---|
| 4,512,827 A | | 4/1985 | Gill |
| 4,731,127 A | | 3/1988 | Itoyama |
| 4,732,619 A | | 3/1988 | Nanigian |
| 5,111,002 A | | 5/1992 | Hollander |
| 5,423,808 A | | 6/1995 | Edwards et al. |
| 5,456,682 A | * | 10/1995 | Edwards ............... A61B 18/00 600/549 |
| 5,464,485 A | * | 11/1995 | Hall, Jr. ............... G01K 7/06 136/230 |
| 5,606,974 A | | 3/1997 | Castellano et al. |
| 5,718,701 A | | 2/1998 | Shai et al. |
| 5,853,409 A | * | 12/1998 | Swanson ............... A61B 18/00 606/31 |
| 6,049,737 A | | 4/2000 | Simpson et al. |
| 6,120,476 A | * | 9/2000 | Fung ............... A61B 18/1492 604/528 |
| 6,176,857 B1 | * | 1/2001 | Ashley ............... A61B 18/08 606/32 |
| 6,830,374 B1 | | 12/2004 | Gray |
| 8,215,955 B2 | | 7/2012 | Lee |
| 10,285,754 B2 | | 5/2019 | Beeckler |
| 2002/0165534 A1 | | 11/2002 | Hayzelden et al. |

FOREIGN PATENT DOCUMENTS

| | | |
|---|---|---|
| CN | 103654947 A | 3/2014 |
| DE | 2454620 B1 | 2/1976 |
| EP | 0 113 554 | 7/1984 |
| EP | 0 928 600 | 7/1999 |
| JP | H05-299703 A | 11/1993 |
| JP | H09-502259 A | 3/1997 |
| JP | 2004-148131 A | 5/2004 |
| JP | 2010-060445 | 3/2010 |
| WO | WO 95/01656 | 1/1995 |
| WO | WO 1996/041654 A1 | 12/1996 |
| WO | WO 2015/041315 A1 | 3/2015 |

OTHER PUBLICATIONS

European Search Report dated Dec. 5, 2016 from corresponding European Patent Application No. 16169868.3.
Chinese Office Action and Search Report dated Apr. 10, 2020 for Application No. 201610329891.4, 15 pages.
European Commumcation dated Oct. 24, 2019 for Application No. 16169868.3, 5 pages.
Japanese Office Action dated Feb. 27, 2020 for Application No. 2016-098608, 6 pages.
Chinese Office Action dated Sep. 23, 2020 for Application No. 201610329891.4, 9 pages.
Japanese Notification of Reasons for Refusal dated Oct. 27, 2020 for Application No. 2016-098608, 4 pages.

* cited by examiner

FIG. 6

CATHETER WITH COAXIAL THERMOCOUPLE

CROSS-REFERENCE TO RELATED APPLICATION

This application is a continuation application of U.S. patent application Ser. No. 14/714,904, filed May 18, 2015, entitled "Catheter with Coaxial Thermocouple," issued as U.S. Pat. No. 10,285,754 on May 14, 2019, the entire contents of which is hereby incorporated by reference.

FIELD OF INVENTION

This invention relates to catheters and electrophysiologic catheters, in particular, catheters for cardiac tissue ablation and diagnostics.

BACKGROUND

Radiofrequency (RF) ablation of cardiac and other tissue is a well-known method for creating thermal injury lesions at the tip of an electrode. Radiofrequency current is delivered between a skin (ground) patch and the electrode, or between two electrodes. Electrical resistance at the electrode-tissue interface results in direct resistive heating of a small area, the size of which depends upon the size of the electrode, electrode tissue contact area, and current (density). Further tissue heating results from conduction of heat within the tissue to a larger zone. Tissue heated beyond a threshold of approximately 50-55 degrees C. is irreversibly injured (ablated).

Resistive heating is caused by energy absorption due to electrical resistance. Energy absorption is related to the square of current density and inversely with tissue conductivity. Current density varies with contact area conductivity, voltage and inversely with the square of the distance from the ablating electrode. Therefore, energy absorption varies with conductivity, the square of applied voltage, and inversely with the fourth power of the distance from the electrode. Resistive heating, therefore, is most heavily influenced by distance, and penetrates a very small distance from the ablating electrode. The rest of the lesion is created by thermal conduction from the area of resistive heating. This imposes a limit on the size of ablation lesions that can be delivered from a surface electrode.

Theoretical methods to increase lesion size would include increasing electrode size, increasing the area of electrode contact with tissue, increasing tissue conductivity and penetrating the tissue to achieve greater depth and increase the area of contact, and delivering RF until maximal lesion size has been achieved (60-90 seconds for full maturation).

The electrode can be introduced to the tissue of interest directly (for superficial/skin structures), surgically, endoscopically, laparoscopically or using percutaneous transvascular (catheter-based) access. Catheter ablation is a well-described and commonly performed method by which many cardiac arrhythmias are treated.

Catheter ablation is sometimes limited by insufficient lesion size. Ablation of tissue from an endovascular approach results not only in heating of tissue, but heating of the electrode. When the electrode reaches critical temperatures, denaturation of blood proteins causes coagulum formation. Impedance can then rise and limit current delivery. Within tissue, overheating can cause steam bubble formation (steam "pops") with risk of uncontrolled tissue destruction or undesirable perforation of bodily structures. In cardiac ablation, clinical success is sometimes hampered by inadequate lesion depth and transverse diameter even when using catheters with active cooling of the tip. Theoretical solutions have included increasing the electrode size (increasing contact surface and increasing convective cooling by blood flow), improving electrode-tissue contact, actively cooling the electrode with fluid infusion, changing the material composition of the electrode to improve current delivery to tissue, and pulsing current delivery to allow intermittent cooling.

Conventional catheters are equipped to measure temperature at their distal sections which are adapted for contact with tissue. Typically, these catheters include a thermocouple wire pair 80 and 82 that extend from the control handle, through the catheter shaft and into the distal section where a "hot" or temperature measuring junction H of the wire pair is positioned. As shown in FIG. 3B, the wire pair 80 and 82 are typically stripped of insulating cover 85, twisted, soldered and potted in a blind hole 86 formed in a distal tip electrode 84, as known in the art. However, because the wire pair 80 and 82 are stripped, twisted and normally bent back on itself with a U-turn 88, the precise location of the distal end "hot" junction H within the blind hole 86 or relative to the tip electrode 84 is not known, even though the depth of the blind hole 86 may be known. An alternate method of assembly includes laser stripping the insulation of a small area of the bifilar wire and then soldering the wires together in that location. Both methods of forming a thermocouple junction are limited in their ability to form a junction at the very bottom of a blind hole. The exact location of the thermocouple junction is the proximal location where the wires are electrically connected. Thus, the location where the temperature is actually measured is by design limited to at least the axial length of the solder joint. For certain types of catheters, it is desirable to have location accuracy of the hot junction down to at least tenths of millimeters and place the thermocouple junction as deep into the hole as possible. Thus, there is a desire for a catheter with a temperature sensor where a more precise location is known of where the temperature is being sensed. Moreover, the conventional thermocouple wire pair has an awkward profile, as shown in FIG. 3C, which can often split or tear between the two wires.

Thus, there is a desire for a catheter with a temperature sensor with a more precise location of its temperature sensing element. In particular, there is a desire for a catheter with a thermocouple wire pair having a more precise location of its "hot" junction, an improved profile, a more durable construction, and an easier method of assembly. Where space is always a constraint within a catheter, there is a further desire for a catheter with a thinner thermocouple wire pair.

SUMMARY OF THE INVENTION

The present invention is directed to a temperature sensor having a more precise temperature sensing location. The temperature sensor includes a coaxial thermocouple wire pair having a more precise "hot" junction at which a first and second metallic material electrically connect with each other for measuring temperature.

In one embodiment, the present invention includes a temperature sensing tensile member for use with a medical device, for example, an electrophysiologic catheter, comprising an elongated body having a proximal end and a distal end. The body includes a core of a first metallic material, the core defining a longitudinal axis, a first coaxial layer of insulating material circumferentially surrounding the core, and a second coaxial layer of a second metallic material circumferentially surrounding the first layer, the second metallic material being different from the first metallic material, the first layer of insulating material electrically insulating the core and second layer from each other along the length of the body and a second layer of insulating material surrounding the assembly and electrically insulating the assembly from the environment. The member further including a solder cap on the distal end, the solder cap electrically connecting the core and the second layer at the distal end.

In a more detailed embodiment, the core includes constantan and the second layer includes copper, or vice versa, and the insulating material includes ceramic and/or a polymer.

In a more detailed embodiment, the member further comprises an outer protective sheath that is electrically nonconductive.

In a more detailed embodiment, the body has been drawn through a die.

The present invention is also directed to an electrophysiologic catheter comprising an elongated catheter body, a distal electrode member, and a temperature sensor having a tensile body, the tensile body extending through the catheter body and having at least a distal end received in the distal electrode member. The temperature sensor comprising a core of a first metallic material defining a longitudinal axis, a coaxial insulating material circumferentially surrounding the core, a coaxial layer of a second metallic material circumferentially surrounding the insulating material, a coaxial insulating material circumferentially surrounding the assembly; and a solder cap on the distal end of the tensile body, the solder cap electrically connecting the core and the layer.

In a more detailed embodiment, the body has been drawn through a die and the coaxial insulating material includes ceramic particulates.

The present invention further includes a method of manufacturing a coaxial thermocouple wire pair member adapted for use with an electrophysiologic catheter, comprising providing a core of a first metallic material defining a longitudinal axis, coaxially surrounding the core with an insulating ceramic material, coaxially surrounding the insulating material with a second metallic material different from the first metallic material, drawing the member through a die, insulating the assembly with a polymer coating, and applying solder on a distal end of the member to electrically connecting the core and the layer at the distal end.

In a more detailed embodiment, the method includes trimming the distal end to expose the core and the layer after drawing the member through a die and before applying solder on the distal end.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1A:
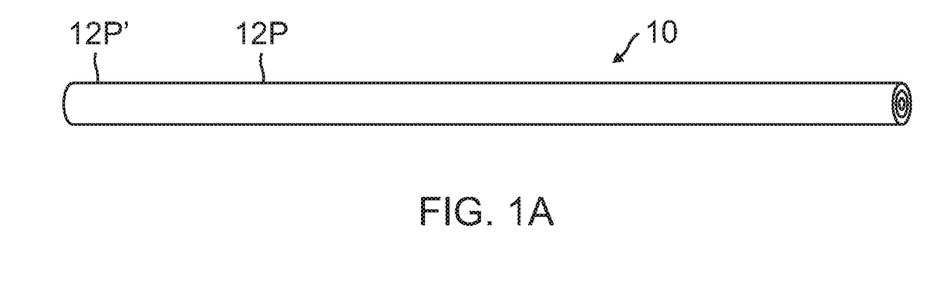
FIG. 1A is a perspective view of a drawn layered member of the present invention, in accordance with one embodiment.
Figure 1B:
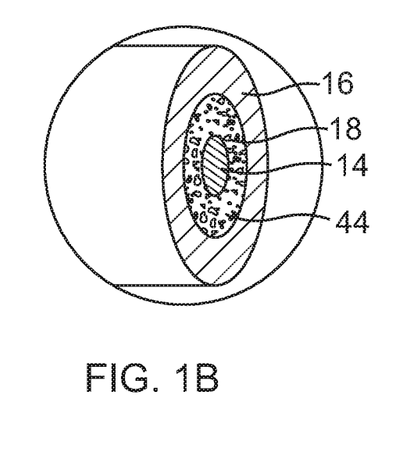
FIG. 1B is a detailed view of an end of the drawn layered member of FIG. 1A.
Figure 2A:
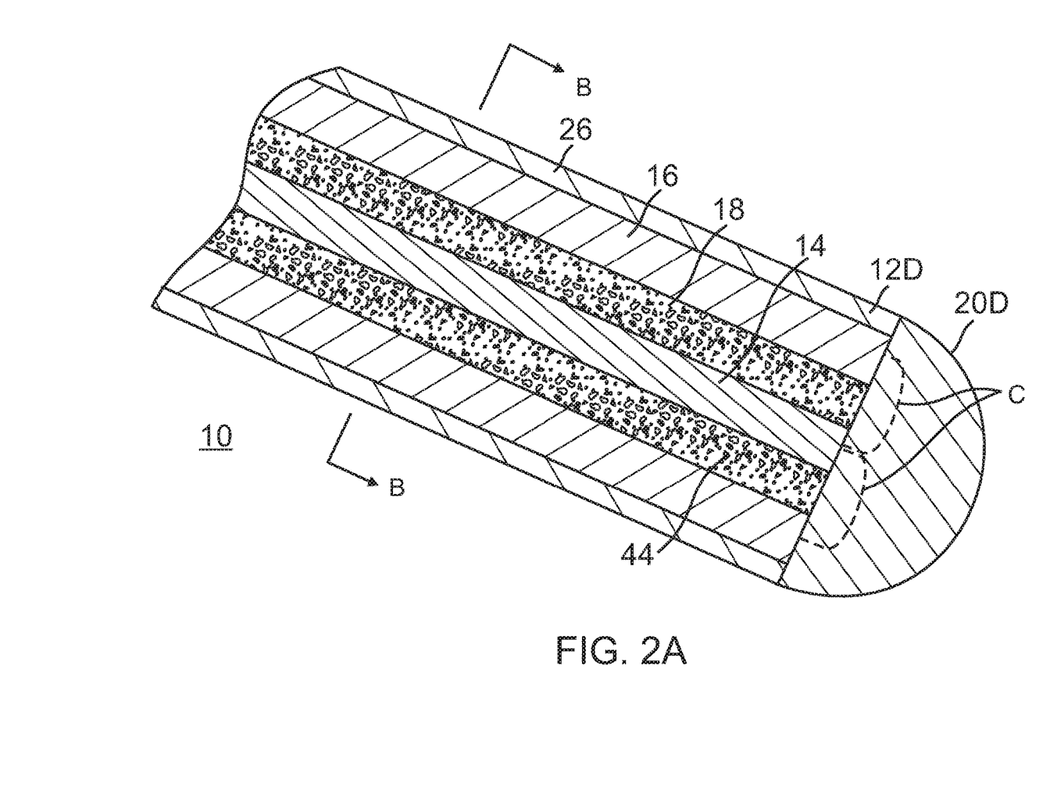
FIG. 2A is a side cross-sectional view of a drawn layered member, including a solder cap on a distal end, forming a drawn thermocouple wire pair member of the present invention, in accordance with one embodiment.
Figure 2B:
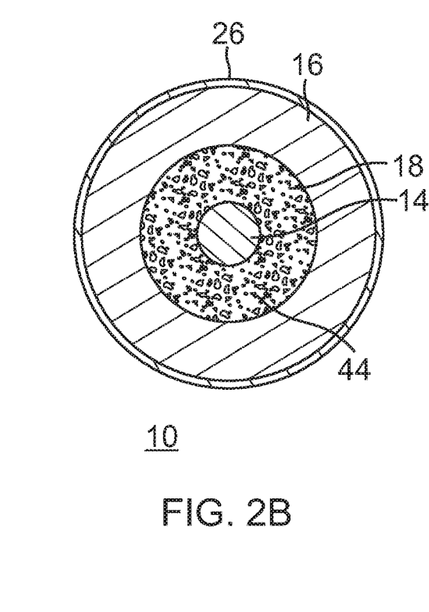
FIG. 2B is an end cross-sectional view of the drawn layered member of FIG. 2A, taken along line B-B.

With reference to FIGS. 1, 2A and 2B, a drawn thermocouple coaxial wire pair member 10 of the present invention includes a single elongated tensile body 12 with a generally circular cross-section. The member 10 has an electrically-conductive core 14 defining a longitudinal axis of the body 12. The core 14 includes a metallic material as a first wire of the wire pair. The member 10 also has an electrically-conductive coaxial layer 16 that includes a different or dissimilar metallic material as a second wire of the wire pair. Advantageously, extending along the length of the body 12, between the metallic core 14 and the metallic layer 16, is an electrically insulating layer 18 that surrounds the core 14 and separates and isolates it from the layer 16. The core 14 and the metallic layer 16 may be of any suitable metals, including, for example, constantan and copper, or vice versa. The insulating layer 18 may be of any suitable material, including, for example, ceramic. An electrically insulating outer sheath 26 may be provided over the entirety of the member. With a coaxial construction providing a generally circular cross-section, as shown in FIG. 2B, the member 10 has an improved profile in terms of utility, convenience and aesthetics. The metallic materials for the first and second wires of the member 10 may be copper and constantan, or vice versa. Alternately, they may be any other dissimilar metals that form a thermocouple. The insulating layer 18 may be constructed of any suitable material, including, for example, a polymer and/or ceramic. The insulating sheath 26 may be constructed of any suitable material, including, for example, a polymer. The preferred method of applying sheath 26 would be a film casting method used to insulate magnet wires, as shown in the art.

Figure 2C:
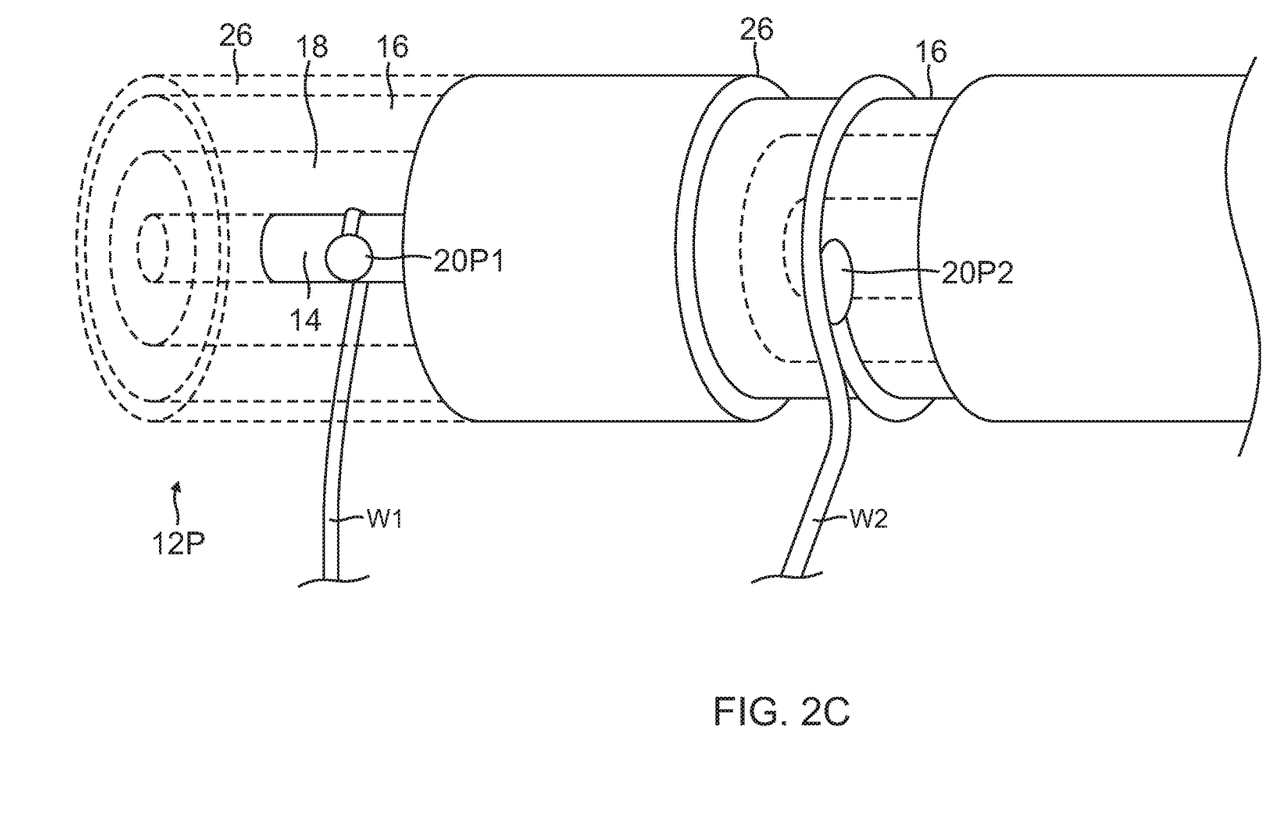
FIG. 2C is a side view of the drawn layered member of FIG. 2, including a soldered proximal end, in accordance with an embodiment.

As shown in FIG. 2A, distal end 12D of the member 10 has a solder cap 20D of a filler metal forming a distal junction of a circuit C between the core 14 and the layer 16. As a "hot" or "measuring junction," the distal solder cap 20D is adapted for measuring temperature of tissue. Proximally, the two conductive layers are attached to wires of corresponding material, as shown in FIG. 2C. This can be accomplished by grinding the sheath 26, and the layers 16, and 18 off proximal end 12P of the member 10 (as shown in broken lines) to expose the core 14. Distally to this grinding, the sheath 26 can be removed mechanically or thermally to expose the layer 16. Once exposed, the layers 14 and 16 can be soldered to a circuit or have wires W1 and W2 of corresponding material soldered directly to them at 20P1 and 20P2, respectively. The solders 20P1 and 20P2 used for this attachment and the distal solder cap 20D can be any solder preferred by the industry, but are usually primarily comprised of tin.

Figure 3A:
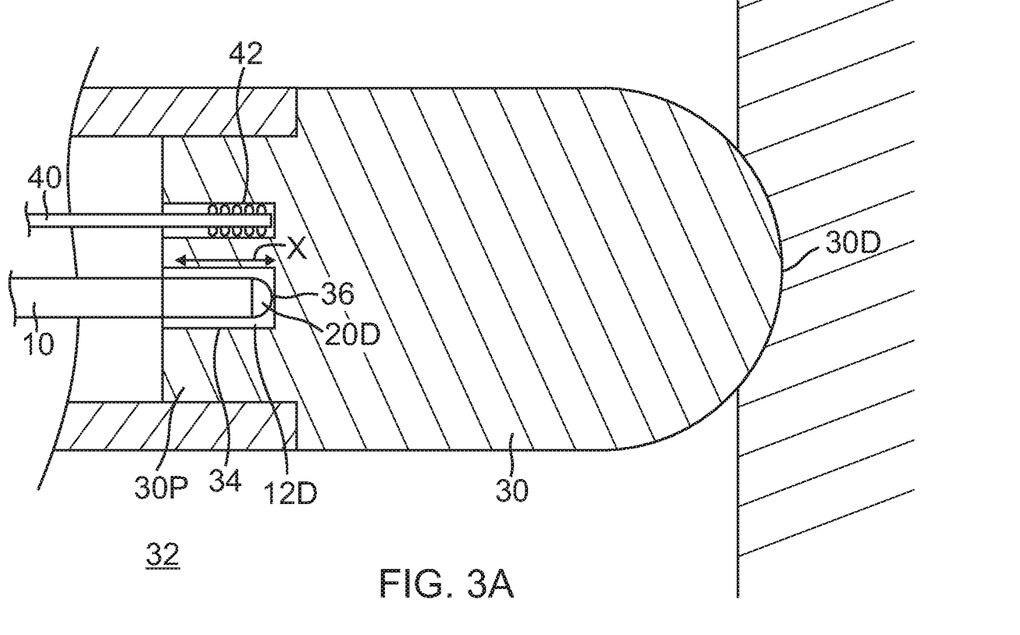
FIG. 3A is a side cross-sectional view of a distal tip section of a catheter of the present invention, with a drawn thermocouple member, in accordance with one embodiment.
Figure 3B:
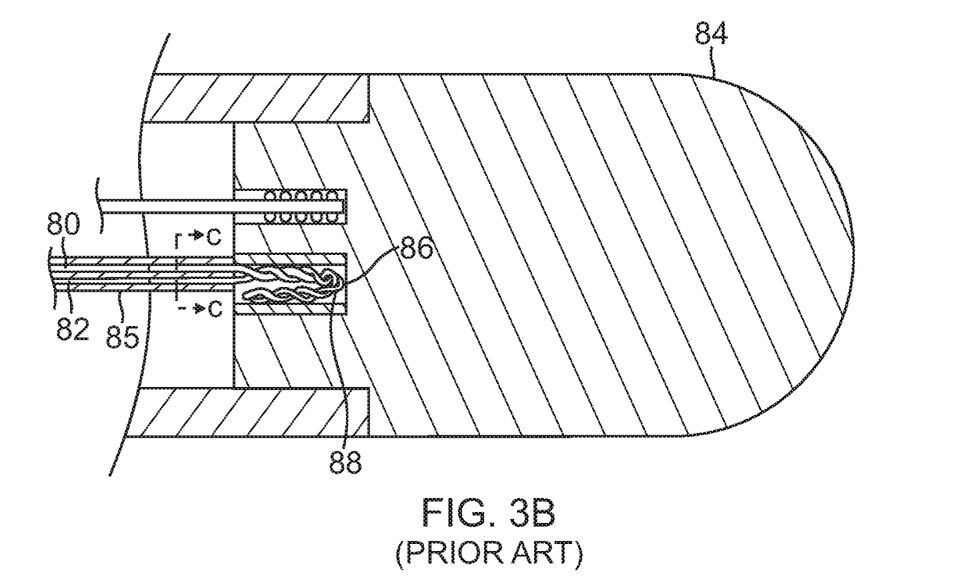
FIG. 3B is a side cross-sectional view of a distal tip section of a conventional catheter of the prior art.
Figure 3C:
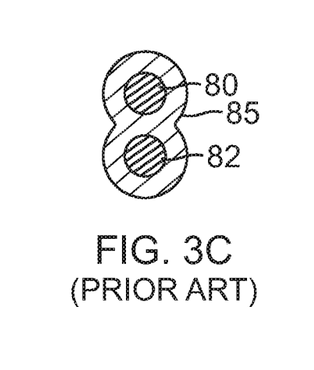
FIG. 3C is an end cross-sectional view of a conventional thermocouple wire pair of FIG. 3C, taken along line C-C.
Figure 4:
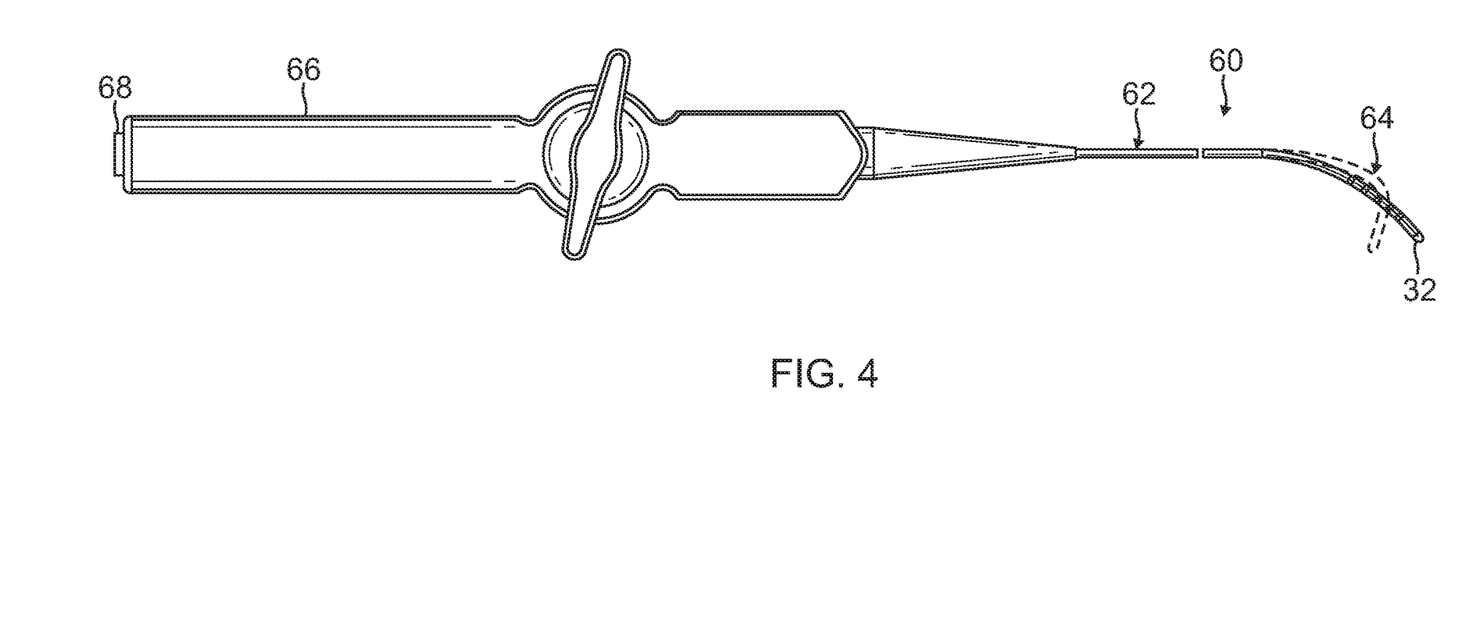
FIG. 4 is a top view of a catheter of the present invention, in accordance with one embodiment.

With reference to FIG. 3A, a catheter distal tip 32 includes a distal tip electrode 30 having a distal end 30D adapted for contact with tissue for diagnostic and/or therapeutic procedures by means of a lead wire 40 whose distal end is anchored and potted in a blind hole 42. The tip electrode 30 also has a proximal end 30P whose face is configured with a blind hole 34 for receiving the distal end 12D and solder cap 20D of the thermocouple wire pair member 10 of the present invention. The blind hole 34 has predetermined and known depth X at an end or "bottom" 36 at which the distal solder cap 20D is placed and potted linearly without any bends or folds in the portion of the member 10 in the hole 34. Thus, the precise location of the distal solder cap 20D (the "hot junction") is known relative to the distal tip electrode when temperature is measured by the member 10 at the distal tip electrode 30. As understood in the art, the member 10 extends through a catheter 60 from the distal tip 32, through a catheter shaft 62 (with a deflection section 64) into a control handle 66 where it is connected to an electrical connector 68 at the proximal end of the handle, as shown in FIG. 4. It is further understood that one or more members 10 may be used with any distal electrode assembly, whether the assembly has a 2-D configuration of a 3-D configuration, for example, circular-, lasso-, basket- or spine-type catheter.

Figure 5:
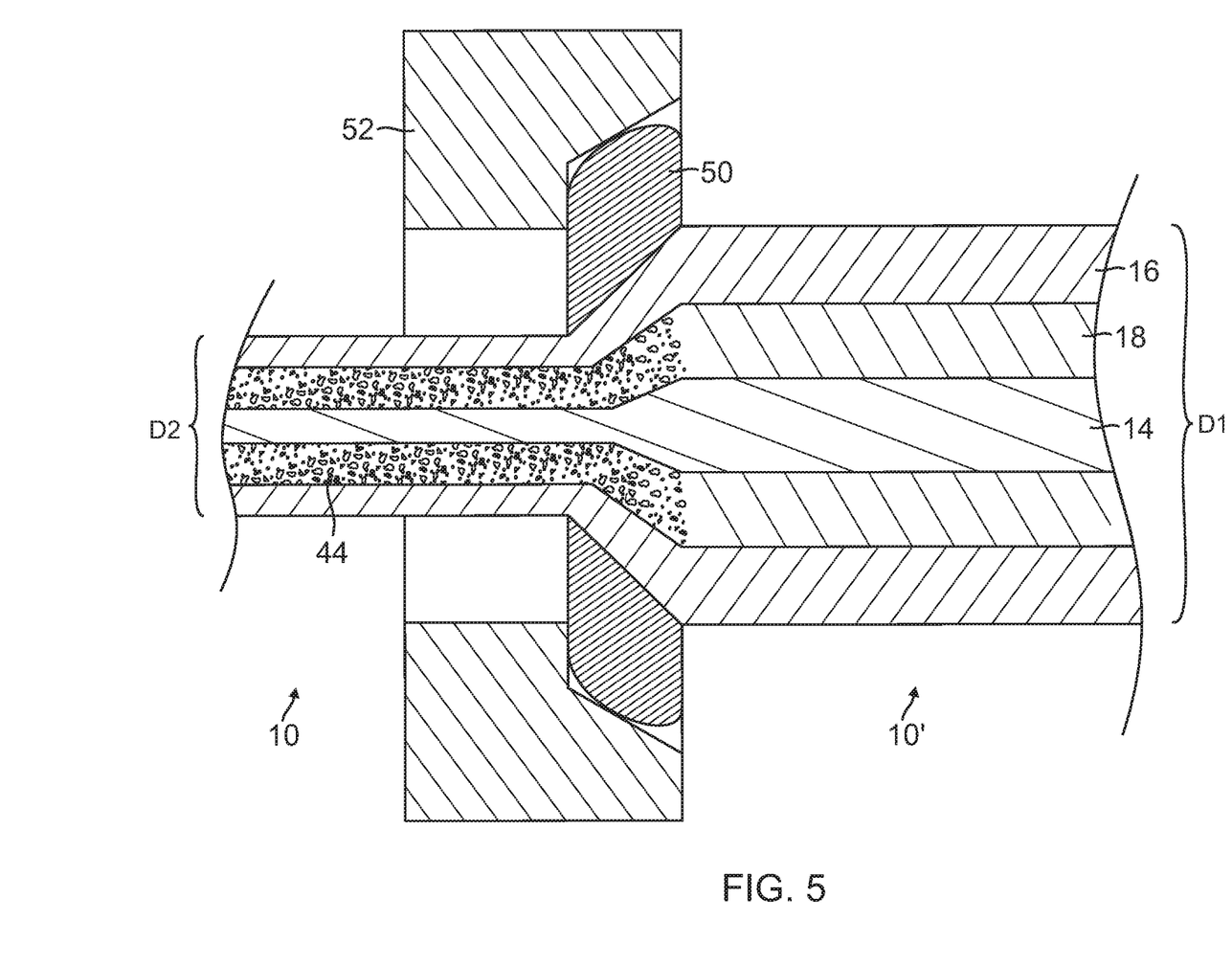
FIG. 5 is a side view of a layered member being drawn, in accordance with a method of manufacture of the present invention.
Figure 6:
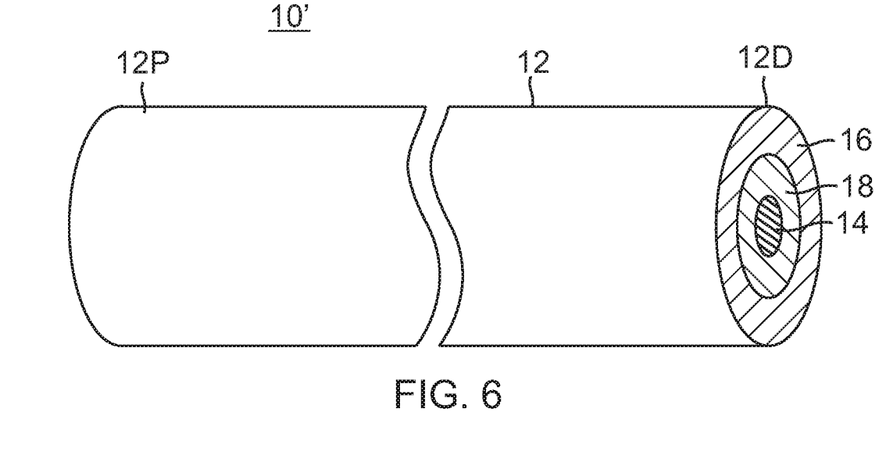
FIG. 6 is a perspective view of a layered member of the present invention prior to drawing.

The present invention includes a method of manufacturing a thermocouple wire pair member 10. The thermocouple wire pair first may be shaped by drawing processes owned and practiced by Fort Wayne Metals Research Products Corporation (Fort Wayne, Ind.), a manufacturer of precision wire-based materials for medical and industrial applications. With reference to FIG. 6, a layered (predrawn) member 10' includes the elongated solid core 14 of a first metallic material which is surrounded circumferentially by a layer of insulating material (e.g., ceramic) forming the insulating layer 18. The core 14 and the layer 18 are surrounded circumferentially by a layer of a second metallic material dissimilar to the first metallic material of the core, forming the outer layer 16. The member 10' may be assembled with the core 14 configured as a solid rod that is inserted into a first, inner hollow tube as the layer 18, and then together into a second, outer hollow tube as the layer 16. With reference to FIG. 5, the member 10', as described above, having an original outer diameter D1 is passed through a die 50 adapted to receive an end of the member 10' to draw it into desired shape and size, including a resulting drawn smaller outer diameter D2. A die holder 52 is provided to hold the die 50. The drawing process may be "cold" or "hot" drawn as desired or appropriate. The member 10' may be pushed and/or pulled through the die 50, as known in the art. As the member 10' is drawn through the die, any or all of the core 14 and the layers 16, and 18 are reshaped, for example, thinned and stretched into the drawn member 10. Where the insulating layer 18 is ceramic, the ceramic is crushed or otherwise broken into smaller particles. After repeated drawing, the ceramic may be crushed into powder form 44. Typically, the drawing process would be for multiple thousands of feet at a time. As shown in FIG. 6, the formed member comprising the core 14 and the layers 18, and 16 can then be run through a multiple layer coating process, i.e. film cast, to apply an insulating polymer layer to the outside.

After the member 10' has been drawn into the member 10 with an elongated body 12 with a desirable diameter, the distal end 12D is prepared for a solder cap by being trimmed to expose the core 14 and the layer 16, and dipped in solder to form distal solder cap 20D, as shown i FIG. 2A. Preferably, the distal solder cap 20D does not extend radially past the outer sheath 26. In other words, the solder cap 20D has a diameter no greater than the diameter of the drawn member 10 with the outer sheath 26. As shown in FIG. 2C, the proximal end 12P is also prepared for soldering by removal of all layers, including the coating 26, and the layers 16 and 18 to expose the core, and at a slightly more distal location removal of the all layers, including the coating 26, to expose the layer 16, and soldering wires W1 and W2 of corresponding materials to the exposed core 14 and the exposed layer 16, respectively.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of one or more embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A medical device having a temperature sensing tensile member, comprising:
   (a) a distal tip electrode having a distal end and a proximal end, the distal end configured to contact and ablate tissue for therapeutic procedures, the proximal end having first and second blind holes, the second blind hole having a known depth;
   (b) a lead wire configured to deliver ablative energy to the tip electrode, wherein the distal end of the lead wire is anchored in the first blind hole; and
   (c) an elongated body configured to sense a temperature of the distal tip electrode, the elongated body having a proximal end and a distal end and comprising:
   (i) a core of a first metallic material, the core defining a longitudinal axis,
   (ii) a first coaxial layer of ceramic material circumferentially surrounding the core,
   (iii) a second coaxial layer of a second metallic material circumferentially surrounding the first coaxial layer, the second metallic material being different from the first metallic material, the first coaxial layer electrically insulating the core and second coaxial layer from each other along the length of the body, and
   (iv) a solder cap on the distal end, the solder cap electrically connecting the core and the second coaxial layer at the distal end, wherein the core and the second coaxial layer form a hot junction of a thermocouple, wherein the distal end of the elongate body is potted linearly without any folds in the second blind hole such that the solder cap is in contact with the bottom of the blind hole, and configured such that the precise location of the distal solder cap is known relative to the distal tip electrode when temperature is measured by the elongated body.

2. The medical device having a temperature sensing tensile member of claim 1, wherein the core includes constantan and the second coaxial layer includes copper.

3. The medical device having a temperature sensing tensile member of claim 1, wherein the core includes copper and the second coaxial layer includes constantan.

4. The medical device having a temperature sensing tensile member of claim 1, wherein the ceramic material is in a powder form.

5. The medical device having a temperature sensing tensile member of claim 1, further comprising an outer protective sheath.

6. The medical device having a temperature sensing tensile member of claim 5, wherein the outer protective sheath is electrically nonconductive.

7. The medical device having a temperature sensing tensile member of claim 1, wherein the first coaxial layer of ceramic material is in a solid form when the elongate body is first assembled, and in a powdered form when the temperature sensing tensile member is first assembled.

8. A medical device comprising:
(a) an elongated catheter body;
(b) a distal electrode member attached to the catheter body and having a proximal end and a distal end, with a blind hole of a known depth in the proximal end; and
(c) a thermocouple having a tensile body, the tensile body extending through the catheter body and having at least a distal end received in the blind hole in the distal electrode member, the thermocouple comprising:
(i) a core of a first metallic material defining a longitudinal axis,
(ii) a coaxial insulating material circumferentially surrounding the core along its length, the coaxial insulating material being a solid annular member prior to the tensile body being drawn through a die in a shaping process, and
(iii) a coaxial layer of a second metallic material circumferentially surrounding the insulating material along its length, and
(iv) a solder cap on the distal end of the tensile body electrically connecting the core and the coaxial layer of the second metallic material, wherein the connection between the core and the coaxial layer of the second metallic material forms a hot junction, wherein the distal end of the thermocouple is potted linearly without any folds in the blind hole such that the solder cap is in contact with the bottom of the blind hole, and configured such that the precise location of the distal solder cap is known relative to the distal tip electrode when temperature is measured by the elongated body.

9. The medical device of claim 8, wherein the core includes constantan and the coaxial layer of the second metallic material includes copper.

10. The medical device of claim 8, wherein the core includes copper and the coaxial layer of the second metallic material includes constantan.

11. The medical device of claim 8, wherein the coaxial insulating material includes ceramic particulates.

12. The medical device of claim 8, further comprising an outer protective sheath.

13. The medical device of claim 12, wherein the outer protective sheath is electrically nonconductive.

14. A medical device comprising:
(a) an elongated catheter body;
(b) a distal electrode member attached to the catheter body and having a proximal end and a distal end, with a blind hole of a known depth in the proximal end; and
(c) a thermocouple having a tensile body, the tensile body extending through the catheter body and having at least a distal end received in the blind hole in the distal electrode member, the thermocouple comprising:
(i) a core of a first metallic material defining a longitudinal axis;
(ii) a coaxial insulating material circumferentially surrounding the core along its length, the coaxial insulating material being a solid annular member prior to the tensile body being drawn through a die in a shaping process; and
(iii) a coaxial layer of a second metallic material circumferentially surrounding the insulating material along its length;
(iv) a solder cap on the distal end of the tensile body electrically connecting the core and the coaxial layer of the second metallic material, wherein the connection between the core and the coaxial layer of the second metallic material forms a hot junction configured for measuring of a temperature, wherein the distal end of the thermocouple is potted linearly in the blind hole and configured such that the precise location of the distal solder cap is known relative to the distal tip electrode when the temperature is measured; and
(v) an outer protective sheath, wherein the outer protective sheath is formed of an electrically nonconductive material.

15. The medical device of claim 14, wherein the core includes constantan and the coaxial layer of the second metallic material includes copper.

16. The medical device of claim 14, wherein the core includes copper and the coaxial layer of the second metallic material includes constantan.

17. The medical device of claim 14, wherein the coaxial insulating material includes ceramic particulates.

18. The medical device of claim 14, wherein the distal end of the thermocouple is potted without any folds in the blind hole.

19. The medical device of claim 18, wherein the solder cap is in contact with the bottom of the blind hole.

20. The medical device of claim 14, wherein the coaxial insulating material is configured to transition to a powdered form upon being drawn through the die in the shaping process.

* * * * *